United States Patent [19]

Frommer et al.

[11] 4,307,194

[45] Dec. 22, 1981

[54] INHIBITORS, OBTAINED FROM BACILLI, FOR GLYCOSIDE HYDROLASES

[75] Inventors: Werner Frommer; Lutz Müller; Delf Schmidt; Walter Puls; Hans-Peter Krause, all of Wuppertal-Elberfeld; Ulrich Heber, Erkrath, all of Fed. Rep. of Germany

[73] Assignee: Bayer Aktiengesellschaft, Leverkusen, Fed. Rep. of Germany

[21] Appl. No.: 858,036

[22] Filed: Dec. 6, 1977

[30] Foreign Application Priority Data

Dec. 23, 1976 [DE] Fed. Rep. of Germany ....... 2658563
Jun. 15, 1977 [DE] Fed. Rep. of Germany ....... 2726899

[51] Int. Cl.³ .......................... C12P 17/12; C12P 1/04
[52] U.S. Cl. .................................. 435/122; 435/170; 435/253; 435/832; 435/839
[58] Field of Search .................. 435/72, 84, 105, 122, 435/184, 253, 832, 839, 170; 546/242

[56] References Cited

U.S. PATENT DOCUMENTS

| | | | |
|---|---|---|---|
| 3,940,479 | 2/1976 | Shomura et al. | 435/838 |
| 4,013,510 | 3/1977 | Frommer et al. | 435/184 |
| 4,019,960 | 4/1977 | Frommer et al. | 435/184 |
| 4,065,562 | 12/1977 | Ohata et al. | 546/242 |
| 4,137,231 | 1/1979 | Murai et al. | 546/242 |
| 4,220,782 | 9/1980 | Stoltefuss | 546/242 |

OTHER PUBLICATIONS

Ishida et al., *J. Antibiotics* (Tokyo), Sera, 20, 66, 1967.
Inouye et al., *Tetrahedron*, 23, 2125–2144, 1968.

*Primary Examiner*—Peter A. Hruskoci

[57] ABSTRACT

According to the present invention inhibitors for glycoside hydrolases, and in particular glucosidase inhibitors especially saccharase inhibitors, which are active in the digestive tract are formed by culturing organisms of the family Bacillaceae, particularly by strains of the genus Bacillus.

It has also been found that certain strains of organisms of the family Bacillaceae, especially strains DSM 7, DSM 704 and DSM 675 produce the antibiotic known as 1-desoxynojirimycin. The invention therefore provides a method of producing 1-desoxynojirimycin which comprises culturing a 1-desoxynojirimycin producing organism of the genus Bacillus. Inhibitors for glycoside hydrolases and the invention includes methods for producing such inhibitors, pharmaceutical compositions containing the inhibitors and methods of treatment involving the use of the inhibitors.

9 Claims, No Drawings

INHIBITORS, OBTAINED FROM BACILLI, FOR GLYCOSIDE HYDROLASES

It is known that a number of organisms of the family actinomycetes, above all Actinoplanaceae, form inhibitors for glycoside hydrolases, preferably carbohydrate-splitting enzymes of the digestive tract (DT-OS (German Published Specification) 2,064,092).

Furthermore, it is known that nojirimycin, an antibiotic having a bacteriostatic action, derived from strains of organisms of the genus Streptomyces, inhibits certain microbial α-glucosidases (T. NIWA et al. Agr. Biol. Chem. 34, 966 (1979)).

According to the present invention inhibitors for glycoside hydrolases, and in particular glucosidase inhibitors especially saccharase inhibitors, which are active in the digestive track are formed by culturing organisms of the family Bacillaceae, particularly by strains of the genus Bacillus.

In addition, we have also found that certain strains of organisms of the family Bacillaceae, especially strains DSM 7, DSM 704 and DSM 675 produce the antibiotic known as 1-desoxynojirimycin. The invention therefore provides a method of producing 1-desoxynojirimycin which comprises culturing a 1-desoxynojirimycin producing organism of the genus Bacillus.

The methods described below are used to discover suitable strains used in the method of the invention.

Strains of the family Bacillaceae, in particular those of the genus Bacillus, are isolated from samples of earth in a known manner. Culture flasks containing nutrient solutions which make growth of these strains possible are inoculated with transinoculation of these strains. For example, it is possible to use a nutrient solution which contains 5 g of peptone and 3 g of meat extract per liter, but in principle many other types of nutrient solutions containing suitable carbon and nitrogen sources and nutrient salts can be employed. The pH value of the nutrient solutions can vary within wide limits; an initial pH of the nutrient solution between 6.0 and 8.0 is preferably chosen.

The most diverse organic substances can be used as the substance which supplies carbon in the nutrient solution. Carbohydrates, organic acids and alcohols may be mentioned as examples.

Yeast extract, soya bean flour, peptones, meat extract and many other organic substances can be used as a nitrogen source as well as suitable aorganic nitrogen sources.

The concentrations of the carbon and nitrogen sources and of the nutrient salts, of which $FeSO_4$, $CaCO_3$ and $MgSO_4$ may be mentioned as examples, can vary within wide limits. In some cases a separate addition of nutrient salts can be dispensed with completely since they are often contained, as concomitant materials, in the complex nitrogen sources.

Since the formation of inhibitors often greatly depends on the composition of the nutrient medium, it is advisable to culture the strains in different nutrient solutions in order to optimise the productive capacity. Appropriate proposals can be seen from the examples.

100-200 ml, for example, of the nutrient solution are filled into a 1 liter conical flask, sterilised in a known manner and inoculated with the strain to be investigated, and the flasks are incubated at about 15°-80° C., preferably at about 24°-40° C. or about 50°-70° C. in the case of thermophilic bacilli, on shaking machines. If the culture exhibits growth, which is in generally visible after 1-10 days, usually after 1-5 days, a sample of, for example, 5 ml is removed and the cells in this sample are separated off by filtration of centrifugation. 1-100 μl of the culture broths are used in the test described in the following text and the inhibiting capacity per ml is calculated.

The cells extracted twice with 5 volumes each time (relative to the cell volume) of acetone and are then extracted once with 5 volumes of diethyl ether. The combined extracts are concentrated to dryness, taken up in water and lyophilised. The lyophilisates are employed in the tests, described in the following text, in concentrations of 10-1,000 μg/ml.

Amylase test

An amylase inhibitor unit (1 AIU) is defined as the amount of inhibitor which inhibits two amylase units to the extent of 50%. An amylase unit (AU) is the amount of enzyme which, under the test conditions indicated below, splits 1 μ equivalent of glucosidic bonds in the starch in one minute. The μ equivalents of split bonds are determined colorimetrically with dinitrosalicylic acid as μ-equivalents of reducing sugar formed and with the aid of a maltose standard curve are given as μ-equivalents of maltose equivalents. In order to carry out the test, 10-1,000 μg of inhibitor, or 1-100 μl of the culture solution to be tested, in 0.4 ml of 0.02 M sodium glycerophosphate buffer/0.001 M $CaCl_2$ of pH 6.9 are added to 0.1 ml of amylase solution (20-22 AU/ml) and the mixture is equilibrated for about 10-20 minutes in a water bath at 35° C. It is then incubated for 5 minutes at 35° C. with 0.5 ml of a 1% strength starch solution, prewarmed to 35° C., and 1 ml of dinitrosalicylic acid reagent (according to P. Bernfeld in Colowick-Kaplan, Meth. Enzymol., volume 1, page 149) is then added. In order to develop the colour, the batch is heated on a boiling water bath for 5 minutes and then cooled and 10 ml of distilled water are added. The extinction at 540 nm is measured against a blank value, without amylase, which has been prepared correspondingly. For evaluation, the amylase activity which is still effective after the addition of inhibitor is read off from an amylase standard curve which has previously been recorded and the percentage inhibition of the amylase employed is calculated from this value. The percentage inhibition is plotted as a function of the quotient $$\frac{\mu g \text{ of inhibitor*}}{AU^{**}},$$

*relative to the dry substance
**$AU$ in the batch of the same series which has not been inhibited, the 50% inhibition point is read off from the curve and converted to AIU/mg of inhibitor.

Saccharase test

A saccharase inhibitor unit (SIU) is defined as the amount of inhibitor which inhibits two saccharase units to the extent of 50%. A saccharase unit (SU) is the amount of enzyme which, under the test conditions indicated below, splits 1 μmol of sucrose into glucose and fructose in one minute. The μmols of glucose formed are determined quantitatively with the aid of the glucose oxidase reaction under conditions under which further splitting of sucrose by saccharase no longer takes place. In order to carry out the test, 1-20 μg of inhibitor, or 1-20 μl of the solution to be tested, are added to 0.05 ml of saccharase solution adjusted to a content of 0.12 SU and the mixture is made up to 0.1 ml with 0.1 M sodium maleate buffer of pH 6.0. Suitably, a solubilised saccharase from swine small intestine mucosa according to B. Borgstrom, A. Dahlquist, Acta Chem. Scand. 12, (1958), page 1,997, is used, diluted to the appropriate SU content with 0.1 M sodium maleate buffer of pH 6.0. The mixture is equilibrated at 35° C. for 10 minutes and 0.1 ml of a 0.05 M sucrose solution in 0.1 M sodium maleate buffer of pH 6.0, prewarmed to 35° C., is then added. The mixture is incubated at 35° C. for 20 minutes and the saccharase reaction is stopped by adding 1 ml of glucose oxidase reagent and the mixture is incubated for a further 30 minutes at 35° C. Suitably, the glucose oxidase reagent is prepared by dissolving 2 mg of glucose oxidase (Messrs. Boehringer, degree of purity I) in 100 ml of 0.565 M tris-HCl buffer of pH 7.0 and subsequently adding 1 ml of detergent solution (2 g of Triton X 100+8 g of 95% strength ethanol, analytical grade), 1 ml of dianisidine solution (260 mg of o-dianisidine 0.2 HCl in 20 ml of $H_2O$) and 0.5 ml of a 0.1% strength aqueous solution of peroxidase (Messrs. Boehringer, lyophilisate, degree of purity II). 1 ml of 50% strength $H_2SO_4$ is then added and the mixture is measured at 545 nm against a corresponding blank value. For evaluation, the percentage inhibition of the saccharase employed is calculated and converted to SIU/g or SIU/liter from the 50% inhibition point with the aid of a glucose standard curve.

Maltase test

A maltase inhibitor unit (MIU) is defined as the amount of inhibitor which inhibits two maltase units to the extent of 50%. A maltase unit (MU) is the amount of enzyme which, under the test conditions indicated below, splits 1 μmol of maltose into 2 μmols of glucose in one minute. The μmols of glucose formed are determined quantitatively with the aid of the glucose oxidase reaction under conditions under which further splitting of maltose by maltase no longer takes place. In order to carry out the test, 1–20 μg of inhibitor, or 1–20 μl of the solution to be tested, are added to 0.05 ml of a maltase solution adjusted to a content of 0.060–0.070. MU. Suitably, a solubilised maltase from swine small intestine mucosa according to B. Borgstrom and A. Dahlquist, Acta Chem. Scand. 12, (1958), page 1,997 is used, diluted to the appropriate MU content with 0.1 M sodium maleate buffer of pH 6.0. The mixture is made up to 0.1 ml with 0.1 M sodium maleate buffer of pH 6.0, and equilibrated at 35° C. for 10 minutes. 0.1 ml of a 0.05 M maltose solution in 0.1 M sodium maleate buffer of pH 6.0, prewarmed to 35° C., is then added. The mixture is incubated for 20 minutes at 35° C. and the maltase reaction is stopped by adding 1 ml of the glucose oxidase reagent described in the saccharase test procedure and the mixture is incubated for a further 30 minutes at 35° C. 1 ml of 50% strength $H_2SO_4$ is then added and the mixture is measured at 545 nm against a corresponding blank value.

For evaluation, the percentage inhibition of the maltase employed is calculated and converted to MIU/g or MIU/liter from the 50% inhibition point with the aid of glucose standard curve.

A number of strains of the family Bacillaceae was tested by the method described above. Significant inhibiting activities against glycoside hydrolases were found here, in particular in the case of strains of the genus Bacillus. The species *B. subtilis, B. subtilis var. niger, B. amyloliquefaciens, B. longisporus, B. polymyxa* and *B. coagulans* proved to be the most favourable with respect to yield.

The frequency with which strains which proved to be active inhibitors in the tests were found by the method indicated was over 5%. Examples of particularly active strains are listed in Table 1

TABLE 1

| Bacillus strains with a saccharase inhibitor action | |
|---|---|
| Species | Strain No. |
| B.subtilis | DSM 704 (ATCC 31324) |
| B.subtilis var. niger | DSM 675 (ATCC 9372) |
| B.amyloliquefaciens | DSM 7 (ATCC 23 350) |
| B.coagulans | DSM 1 (ATCC 7050) |
| B.longisporus | DSM 479* (ATCC 31323) |
| B.polymyxa | DSM 365 (ATCC 31321) |
| B.polymyxa | DSM 372 (ATCC 31322) |
| B.polymyxa | DSM 742 (ATCC 31327) |
| B.polymyxa | DSM 292 (ATCC 31320) |
| B.polymyxa | DSM 356 (ATCC 8523) |
| B.polymyxa | DSM 36 (ATCC 842) |
| B.polymyxa | DSM 740 (ATCC 31325) |
| B.polymyxa | DSM 741 (ATCC 31326) |
| B.subtilis | DSM 1060 (ATCC 31328) |
| B.subtilis | DSM 1061 (ATCC 31329) |
| B.subtilis | DSM 1062 (ATCC 31330) |
| B.subtilis | DSM 1063 (ATCC 31331) |
| B.subtilis | DSM 1064 (ATCC 31332) |
| B.subtilis | DSM 1065 (ATCC 31333) |
| B.subtilis | DSM 1066 (ATCC 31334) |
| B.subtilis | DSM 1067 (ATCC 31335) |

*also inhibits amylase

The strains listed are deposited under the DSM numbers indicated in the Deutsche Sammlung fur Mikroorganismen (German Collection of Micro-organisms) (DSM), at Gottingan, and can be obtained from there.*)

*The strains are also deposited under the given ATCC numbers in the American Type Culture Collection, Rockville, Md. (USA).

Strains DSM 704, 740, 741 and 742 are new strains. The invention therefore includes an in vitro culture of one of these strains. The properties of these strains are described in Table 2. The remaining strains are known from the literature and are listed in the "Catalogue of Strains 1974" of the DSM.

TABLE 2

| Properties of the strains | DSM 740 | DSM 741 | DSM 742 | DSM 704 |
|---|---|---|---|---|
| Rods length, μ | 3–6 | 2–5 | 3–7 | 2–4 |
| width, μ | 0.6–0.8 | 0.6–0.8 | 0.7–0.8 | 0.6–0.8 |
| Gram reaction | + | ± | ± | + |
| Spores ellipsoidal/cylindrical | + | + | + | + |
| round | − | − | − | − |
| terminal/subterminal | + | + | + | + |
| central/paracentral | + | + | + | + |
| spore mother cell swollen | + | + | + | − |
| Mobility | + | + | + | + |
| Maximum growth temperature | | | | |
| growth positive at °C. | 40 | 40 | 45 | 55 |
| growth negative at °C. | 45 | 45 | 50 | 60 |
| Catalase | + | + | + | + |
| Anaerobic growth | + | + | + | − |
| Maximum growth temperature | | | | |
| growth positive at °C. | 40 | 40 | 45 | 55 |
| growth negative at °C. | 45 | 45 | 50 | 60 |
| Catalase | + | + | + | + |
| Anaerobic growth | + | + | + | − |
| Voges-Proskauer reaction | + | + | + | + |
| pH in VP medium | 6.2 | 6.5 | 6.5 | 5.6 |
| Egg yolk reaction | − | − | − | − |
| Growth | | | | |
| pH 5.7 | + | + | + | + |
| 5% of NaCl | ± | − | − | + |
| 7% of NaCl | − | − | − | + |
| 10 of NaCl | − | − | − | + |
| Lysozym (0.001%) | − | + | − | − |
| Acid formation from | | | | |
| D-glucose | + | + | + | + |
| L-arabinose | + | + | + | + |

TABLE 2-continued

| Properties of the strains | DSM 740 | DSM 741 | DSM 742 | DSM 704 |
|---|---|---|---|---|
| D-xylose | + | + | + | + |
| D-mannitol | + | + | + | + |
| Gas formation from glucose | + | + | + | − |
| Degradation of | | | | |
| starch | + | + | + | + |
| casein | + | + | + | + |
| gelatine | + | + | + | + |
| tyrosine | − | − | − | − |
| hippurate | − | − | − | − |
| pectin | + | + | + | |
| Evaluation of | | | | |
| citrate | − | − | − | + |
| propionate | − | − | − | |
| Desamination of phenylalanine | − | − | − | |
| Reduction of $NO_3^-$ to $NO_2^-$ | + | + | + | + |
| Gas formation from nitrate | − | − | − | − |
| Formation of | | | | |
| crystalline dextrines | − | − | − | |
| indole | − | − | − | − |
| dihydroxyacetone | + | + | − | |

Because of spore formation and aerobic growth, the strains DSM 740, DSM 741, DSM 742 and DSM 704 are to be assigned to the genus Bacillus. The morphological and physiological characteristics determined of the strains DSM 740, DSM 741 and DSM 742 correspond to those of Bacillus polymyxa, whilst the strain DSM 704 is to be assigned to the species *Bacillus subtilis*.

The identification was carried out according to the instructions of R. E. Gordon, W. C. Haynes and C. Hor-Nay Pong: The Genus Bacillus, Washington 1973.

In order to obtain the glycoside hydrolase inhibitors, the strains listed above are cultured in a nutrient solution for example, as described above. Cultures of the organisms used in this invention generally comprise, in addition to the organism, a nutrient medium containing sources of carbon and nitrogen. It should be borne in mind however that virtually every strain will require a nutrient solution of different qualitative composition and a different quantitative composition of optimum production.

In general, the organism is incubating for 1-10 days at 15°-80° C., preferably 24°-40° C. or, in the case of thermophiles, 50°-70° C., in shaking flasks or in fermenters of varying size. The cells are then separated off from the culture solution and, depending on the occurrence of the inhibitors, the active compound is concentrated from the culture solution and/or from the cells.

The inhibitors are isolated from the culture broths by lyophilisation or precipitation with salts or water-soluble organic solvents (such as, for example, lower alcohols and ketones) or by adsorption of the active compounds on ion exchangers.

The inhibitors are isolated from the cells by extraction with organic solvents, such as, for example, alcohols, ketones, ethers, esters and sulphoxides.

For this, the fermentation batch is centrifuged at 3,000-20,000 rpm, preferably 6-10,000 rpm, for 10-60 minutes, preferably 30 minutes, or filtered, preferably under pressure and with the aid of filtering auxiliaries, and is separated in this manner into culture broth and cell residue.

The isolation of the inhibitor from the particular culture broth can be carried out in various ways:

(a) Concentration of the culture broths under reduced pressure (10-50 mm Hg) at bath temperatures of 20°-100° C., preferably 40°-80° C., to about 1/5-1/50 of the starting volume. The concentrated extract is filtered or centrifuged and the clear filtrate (the clear supernatant liquor) is lyophilised, if appropriate after freeing from salts beforehand.

(b) Precipitation of the inhibitors from the culture broth (or from the culture broths concentrated according to (a)) by adding water-soluble organic solvents, such as, for example, alcohols or ketones, preferably methanol, ethanol or acetone, up to a content of 60-90%. Since inactive concomitant substances are precipitated at a lower concentration of solvent, this precipitation process is particularly suitable for fractional precipitation for separating off undesired concomitant materials.

(c) Salting out of the inhibitors from the extracts (or the extracts concentrated according to (a)), for example with ammonium sulphate, sodium chloride and the like. The precipitate which separates out is collected by centrifugation or filtration and either washed directly with acetone and ether and dried in vacuo or, after redissolving in water, is dialysed and lyophilised.

(d) Adsorption of the inhibitors on ion exchangers. This process is suitable for isolating those inhibitors which, because of their chemical nature, carry charges. The desorption of the inhibitors is effected by altering the ionic strength or the pH value of the elution medium.

In addition to the inhibitor, undesired concomitant substances are frequently present in the culture broths. These concomitant materials can be separated off in various ways, for example by denaturing the concomitant materials by means of heat in the case of inhibitors which are stable towards heat or by dialysis through appropriate membranes in the case of low-molecular inhibitors, the undesired concomitant materials being held back by the membrane, or by fractional precipitation (compare b), or by adsorption of the concomitant materials on ion exchangers.

The inhibitors are isolated from the cells by extracting the cells several times with organic solvents, preferably extracting them twice for 10-20 minutes with 3-5 volumes of acetone (relative to the moist cell volume) and then extracting them once for 5-10 minutes with ether. The acetne extracts and ether extracts are concentrated to dryness in vacuo and the residue is taken up in water and lyophilised.

The new substaces dissolve readily in water. One group of inhibitors is stable towards heat at neutral pH values, stable towards acid (pH 2) and stable towards alkali (pH 12) and can be dialysed. These inhibitors are not inactivated by trypsin and pepsin and in turn they do not inhibit the enzymes mentioned. They cannot be stained with typical protein dyestuffs. According to estimations from gel filtration, the molecular weight of these inhibitors is over 100 but below 2,000.

The best inhibitors of these groups are distinguished by an extremely high inhibiting action against saccharase.

When the strain DSM 7 is fermented in a nutrient solution of composition A (See Example 4), over 400,000 SIU/l are obtained after fermenting for four days and when this strain is cultured in nutrient solution $S_3$ (see Example 3), over 300,000 SIU/l are obtained after fermenting for six days.

A crude inhibitor of about 40,000 SIU/g is obtained by adsorption on strongly acid cation exchangers in the H⊕ form and subsequent desorption with aqueous $NH_3$ solution and concentration and lyophilisation of the desorbate. Extraction of the crude inhibitor with methanol, concentration of the extract to dryness, redissolving the residue in water and chromatography of the aqueous solution on weakly acid exchangers based on dextran or cellulose, in particular carboxymethylcellulose, desorption with dilute mineral acids, preferably $10^{-3}$–$10^{-1}$ N hydrochloric acid, concentration of the fractions having a saccharase inhibitory action and lyophilisation of these fractions leads to an enriched crude product of about 250,000 SIU/g. Chromatography of the enriched crude product on modified dextran (Sephadex ® LH 20) in methanol, concentration of the fractions having a saccharase inhibitory action and addition of concentrated mineral acids, preferably concentrated hydrochloric acid, down to a pH value of 1–3 gives a crystalline product of 540,000 SIU/g. This substance is pure according to chromatography. $C_6H_{13}O_4N$ or, for the hydrochloride, $C_6H_{14}O_4NCl$ was determined as the empirical formula. On the basid of its physical parameters (IR, NMR and UV spectra; melting point; and specific rotation) and the chemical properties (periodate oxidation and elementary analysis), it is identical to a compound of the empirical formula $C_6H_{13}O_4N$ or, for the hydrochloride, $C_6H_{14}O_4NCl$, described by S. INOYE et al. (Tetrahedron 23, 2125 (1968)), to which the structural formula

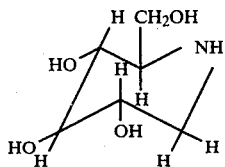

has been assigned by the authors and for which the name "1-desoxynojirimycin" has been proposed.

This compound was obtained by the authors by a chemical route by hydrogenating the antibiotic nojirimycin. The starting product nojirimycin is obtained according to T. NIIDA et al. (J. Antibiotics, Ser. A. 20, 62 (1967)) by fermenting organisms of the genus Streptomyces.

The present invention makes it possible for the first time to prepare desoxynojirimycin in good yields in one operation by direct microbiological synthesis, without using a roundabout route via nojirimycin which is relatively unstable and therefore difficult to handle.

It is exceptionally surprising and was not to be foreseen that these compounds are produced by organisms of the genus Bacillus, since these microorganisms are generally less suitable as producers of secondary substances and at best essentially form peptide-like secondary substances.

Furthermore, individual strains, for example DSM 372, form saccharase inhibitors which, in a mixture, in addition to desoxynojirimycin and/or nojirimycin, also produce other components, having a saccharase inhibiting action, which can be clearly differentiated in a thin layer chromatogram.

Other strains, for example DSM 741, form inhibitors in which no desoynojirimycin or nojirimycin can be detected in a thin layer chromatogram and which are thus of another chemical structure.

It is known that in warm-blooded animals, after intake of carbohydrate-containing foodstuffs and beverages (for example cereal starch, potato starch, fruit, fruit juices, beer and chocolate), hyperglycaemias arise which are brought about as a result of a rapid degradation of the carbohydrates by glycoside hydrolases (for example salivary and pancreatic amylases, maltases and saccharases) according to the following equation

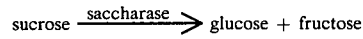

In the case of diabetics, these hyperglycaemias are particularly strong and of long-lasting pronounced character. In the case of adipose subject, the alimentary hyperglycaemia frequently leads to a particularly intense insulin secretion which in turn leads to increased fat synthesis and decreased fat degradation. Following such hyperglycaemias, a hypoglycaemia frequently occurs in the case of adipose persons of sound metabolism, as a result of the insulin secretion. It is known that both hypoglycaemias and foodstuff sludge remaining in the stomach promote the production of gastric juice which in turn causes, or favours, the formation of a gastritis or a gastric or duodenal ulcer.

It is also known that carbohydrates, particularly sucrose, are split in the oral cavity by micro-organisms and the formation of caries is thereby promoted.

Malabsorption of carbohydrates, for example as a result of intestinal saccharase deficiency, causes diarrhea. Suitable doses of a glucosidase inhibitor effect a synthetic malabsorption and are thus suitable for counteracting constipation.

The inhibitors according to the invention are thus suitable for use as therapeutic agents for the following indications: adiposity, hyperlipoproteinaemia, atherosclerosis, diabetes, prediabetes, gastritis, constipation and caries.

In order to broaden the spectrum of activity, it can be advisable to combine inhibitors for glycoside hydrolases which complement one another in their action, the combinations being either combinations of the inhibitors according to the invention with one another or combinations of the inhibitors according to the invention with inhibitors which are already known. Thus, for example, it can be appropriate to combine saccharase inhibitors according to the invention with amylase inhibitors or saccharase inhibitors which are already known.

In some cases, combinations of the inhibitors according to the invention with known oral antidiabetic agents ($\beta$-cytotropic sulphonylurea derivatives and/or biguanides having an action on the blood sugar) and with blood lipid-lowering active compounds, such as, for example, clofibrat, nicotinic acid, cholestyramine and others, are also advantageous.

The compounds can be administered without dilution, for example as a powder or in a gelatine casing, or in combination with an excipient in a pharmaceutical composition.

The present invention therefore provides a pharmaceutical composition containing as active ingredient a compound of the invention in admixture with a solid or liquified gaseous diluent, or in admixture with a liquid diluent other than a solvent of a molecular weight less than 200 (preferably less than 350) except in the presence of a surface active agent.

The invention further provides a pharmaceutical composition containing as active ingredient a compound of the invention in the form of a sterile or isotonic aqueous solution.

The invention also provides a medicament in dosage unit form comprising a compound of the invention.

The invention also provides a medicament in the form of tablets, (including lozenges and granules), dragees, capsules, pills, ampoules or suppositories comprising a compound of the invention.

"Medicament" as used in this Specification means physically discrete coherent portions suitable for medical administration. "Medicament in dosage unit form" as used in this Specification means physically discrete coherent units suitable for medical administration each containing a daily dose or a multiple (up to four times) or sub-multiple (down to a fortieth) of a daily dose of the compound of the invention in association with a carrier and/or enclosed within an envelope. Whether the medicament contains a daily dose or, for example, a half, a third, or a quarter of a daily dose will depend on whether the medicament is to be administered once or, for example, twice, three times or four times a day respectively.

The pharmaceutical compositions according to the invention may, for example, take the form of ointments, gels, pastes, creams, sprays (including aerosols), lotions, suspensions, solutions and emulsions of the active ingredient in aqueous or non-aqueous diluents, syrups, granulates or powders.

The diluents to be used in pharmaceutical compositions (e.g. granulates) adapted to be formed into tablets, dragees, capsules and pills include the following:
(a) fillers and extenders, e.g. starch, sugars, mannitol, and silicic acid; (b) binding agents, e.g. carboxymethyl cellulose and other cellulose derivatives, alignates, gelatine and polyvinyl pyrrolidone; (c) moisturizing agents, e.g. glycerol; (d) disintegrating agents, e.g. agar-agar, calcium carbonate and sodium bicarbonate; (e) agents for retarding dissolution e.g. paraffin; (f) resorption accelerators, e.g. quaternary ammonium compounds; (g) surface active agents, e.g. cetyl alcohol, glycerol monostearate; (h) adsorptive carriers, e.g. knelin and bentonite; (i) lubricants, e.g. talc, calcium and magnesium stearate and solid polyethylene glycols.

The pharmaceutical compositions which are powders can, for example, contain the usual diluents, e.g. lactose, talc, silicic acid, aluminium hydroxide, calcium silicate, and polyamide powder or mixtures of these substances. Aerosol sprays can, for example, contain the usual propellants, e.g. chlorofluorohydrocarbons.

Powder is prepared by comminuting the substance to a suitable size and mixing it with a pharmaceutical excipient, also comminuted. Although an edible carbohydrate, such as, for example, starch, lactose, sucrose or glucose, is usually used for this purpose and can also be used here, it is desirable to use a carbohydrate which cannot be metabolised, such as, for example, a cellullose derivative.

Sweeteners, flavouring additives, preservatives, dispersing agents and dyestuffs can also be present.

The tablets, dragees, capsules and pills formed from the pharmaceutical compositions of the invention can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, of polymeric substances or waxes.

The ingredient can also be made up in microencapsulated form together with one or several of the above-mentioned diluents.

Capsules can be prepared by formulating the powder mixture described above and filling gelatine casings which have already been formed. Lubricants, such as, for example, silica gel, talc, magnesium stearate, calcium stearate or solid polyethylene glycol, can be added to the powder mixture before the filling operation. A disintegrating agent or solubiliser, such as, for example, agar-agar, calcium carbonate or sodium carbonate, can also be added to the mixture in order to improve the accessibility of the inhibitor when the capsule is taken.

Tablets are manufactured, for example, by preparing a powder mixture, coarse or fine-grained, and adding a lubricant and disintegrating agent. Tablets are formed from this mixture. A powder mixture is prepared by mixing the substance which has been communited in a suitable manner, and a diluent or another excipient as described above is added. A binder is optionally added: for example carboxymethylcellulose, alginates, gelatine or polyvinylpyrrolidones, a solution retarder, such as, for example, paraffin, a resorption accelerator, such as, for example, a quaternary salt and/or an adsorbent, such as, for example, bentonite, kaolin or dicalcium phosphate. The powder mixture can be granulated together with a binder, such as, for example, syrup, starch paste or gum acacia, or solutions of cellulose or polymeric materials. Thereafter, the product is pressed through a coarse sieve. Alternatively, it is possible to allow the powder mixture to run through a tablet machine and to comminute the resulting non-uniformly shaped pieces to the particle size. So that the resulting particles do not jam in the tablet-forming nozzles, a lubricant can be added, such as, for example, stearic acid, stearate salt, talc or mineral oil. This mixture which has been lubricated is then pressed into tablet form. The active compounds can also be combined with free-flowing inert excipients and brought directly into tablet form, omitting the granulation or comminution steps. The product can be provided with a clear or opaque protective casing, for example a coating of shellac, a coating of sugar or polymer substances and a polished casing of wax. Dyestuffs can be added to these coatings so that a distinction can be made between the different dosage units.

The pharmaceutical compositions which are solutions and emulsions can, for example, contain the customary diluents (with, of course, the above-mentioned exclusion of solvents having a molecular weight below 200 except in the presence of a surface-active agent), such as solvents, dissolving agents and emulsifiers; specific examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils [for example ground nut oil], glycerol, tetrahydrofurfuryl alcohol, polyethylene glycols and fatty acid esters of sorbitol or mixtures thereof.

The pharmaceutical compositions which are suspensions can contain the usual diluents, such as liquid diluents, e.g. water, ethyl alcohol, propylene glycol, surface-active agents (e.g. ethoxylated isostearyl alcohols, polyoxyethylene sorbite and sorbitane esters), microcrystalline cellulose, aluminium metahydroxide, bentonite, agar-agar and tragacanth or mixtures thereof.

The formulation forms to be administered orally, such as, for example, solutions, syrup and elixirs, can be prepared in dosage units so that a particular amount of formulation contains a particular amount of active compound. The syrup can be prepared by dissolving the active compound in an aqueous solution which contains suitable flavouring substances; elixirs are obtained using non-toxic, alcoholic excipients. Suspensions can be prepared by dispersing the compound in a non-toxic excipient. Solubilisers and emulsifying agents, such as, for example, ethoxylated isostearyl alcohols and polyoxyethylene sorbitol esters, preservatives and additives which improve the flavour, such as, for example, peppermint oil or saccharin and the like, can also be added.

Dosage instructions can be given on the capsule. Moreover, the dosage can be made safe so that the active compound is released in a delayed manner, for example by holding the active compound in polymer substances, waxes or the like.

All the pharmaceutical compositions according to the invention can also contain colouring agents and preservatives as well as perfumes and flavouring additions (e.g. peppermint oil and eucalyptus oil) and sweetening agent (e.g. saccharin).

The pharmaceutical compositions according to the invention generally contain from 0.1 to 99.5, usually from 0.5 to 95% of the active ingredient by weight of the total composition.

In addition to a compound of the invention, the pharmaceutical compositions and medicaments according to the invention can also contain other pharmaceutically active compounds. They may also contain a plurality of compounds of the invention.

Any diluent in the medicaments of the present invention may be any of those mentioned above in relation to the pharmaceutical compositions of the present invention. Such medicaments may include solvents of molecular weight less than 200 as sole diluent.

The discrete coherent portions constituting the medicament according to the invention will generally be adapted by virtue of their shape or packaging, for medical administration and may be, for example, any of the following: tablets, (including lozenges and granulates), pills, dragees, capsules, suppositories and ampoules. Some of these forms may be made up for delayed release of the active ingredient. Some, such as capsules, include a protective envelope which renders the portions of the medicament physically discrete and coherent.

The preferred daily dose for administration of the medicaments of the invention is from about 1500 to $3 \times 10^7$ AIU and from about 50 to $1 \times 10^6$ SIU of active ingredient.

This invention further provides a method of controlling carbohydrate metabolism and/or combating (including prevention, relief and cure of) the above-mentioned diseases in warm-blooded animals, which comprises administering to the animals a compound of the invention alone or in admixture with a diluent or in the form of a medicament according to the invention.

It is envisaged that these active compounds will be administered primarily perorally.

In general it has proved advantageous to administer amounts of from 30 to $3 \times 10^5$ AIU/kg and from 1 to $1 \times 10^4$ SIU/kg of body weight per day to achieve effective results. Nevertheless, it can at times be necessary to deviate from those dosage rates, and in particular to do so as a function of the nature and body weight of the human or animal subject to be treated, the individual reaction of this subject to the treatment, the type of formulation in which the active ingredient is administered and the mode in which the administration is carried out, and the point in the progress of the disease or interval at which it is to be administered. Thus it may in some case suffice to use less than the above-mentioned minimum dosage rate, whilst other cases the upper limit mentioned must be exceeded to achieve the desired results. Where larger amounts are administered it can be advisable to divide these into several individual administrations over the course of the day.

In addition to the abovementioned pharmaceutical compositions, and medicaments, the invention also includes a medicated foodstuff (which may be formulated for consumption by any warm-blooded animals) containing an active compound of the invention and a nutritious material. Examples of such foodstuffs suitable for consumption incude sugar, bread, potato products, fruit juice, beer, chocolate and other confectionary, and preserves, such as, for example, jam, to which a therapeutically active amount of at least one of the inhibitors according to the invention has been added.

Furthermore, the inhibitors according to the invention have the property, in animals, of influencing, to a high degree, the ratio of the proportion of undesired fat to the proportion of desired meat of low fat content (lean meat) in favour of the lean meat. This is of particular importance for the rearing and keeping of agricultural stock animals, for example in the fattening of pigs, but is also of considerable importance for the rearing and keeping of other stock animals and pets. Furthermore, the use of the inhibitors can lead to a considerable rationalisation of the feeding of the animals, both in respect of time, quantity and quality. Since they cause a certain delay in digestion, the residence time of the nutrients in the digestive tract is extended, whereby ad libitum feeding associated with less expense is made possible. Furthermore, in many cases there is a considerable saving of valuable portein feed when the inhibitors according to the invention are used.

The active compounds can thus be used in virtually all sections of animal nutrition as agents for reducing the formation of fatty layers and for the saving of feed protein.

The activity of the active compounds here is essentially independent of the nature and the sex of the animals. The active compounds prove particularly valuable in species of animals which generally tend to deposit relatively large amounts of fat or tend to do so during certain stages of their life.

The following stock animals and pets may be mentioned as examples of animals with which the inhibitors for reducing the formation of fatty layers and/or for saving feed protein can be employed: warm-blooded animals, such as cattle, pigs, horses, sheep, goats, cats, dogs, rabbits, fur-bearing animals, for example mink and chinchillas, and other pets, for example guineapigs and hamsters, laboratory animals and zoo animals, for example rats, mice, monkeys and the like, poultry, for example broilers, chickens, geese, ducks, turkeys and pigeons, parrots and canaries, and cold-blooded animals, such as fish, for example carp, and reptiles, for example snakes.

Because of the favourable properties of the active compounds, the amount of active compounds administered to the animals in order to achieve the desired effect can be substantially varied. It is preferably about 0.5 mg to 2.5 g/kg, in particular 10 to 100 mg/kg, of feed. The period over which the active compound is administered can be from a few hours or days to several years. The appropriate amount of active compound and the appropriate period over which it is administered are closely connected with the object of feeding. In particular, they depend on the nature, the age, the sex and the state of health of the animals and on the method of keeping the animals and can be easily determined by any person skilled in the art.

The active compounds according to the invention are administered to the animals by the customary methods. The nature of the administration depends, in particular, on the nature, the behaviour and the general condition of the animals. This, it is possible to carry out the administration orally once or several times daily, at regular or irregular intervals. In most cases, oral administration, in particular in the rhythm of the food and/or drink intake of the animals, is to be preferred for reasons of expediency.

The active compounds can be administered as pure substances or in the formulated form, the formulated form being understood both as a premix, that is to say mixed with non-toxic inert excipients of any desired nature, and also as part of a total ration in the form of a supplementary feed and as a constituent of the mixture of a mixed feed by itself. Administration of suitable formulations by means of the drinking water is also included.

The active compounds, optionally in the formulated form, can also be administered together with other nutrients and active compounds, for example mineral salts, trace elements, vitamins, proteins, energy carriers (for example starch, sugar or fats), dyestuffs and/or flavouring substances or other feedstuff additives, for example growth promoters, in a suitable form. The active compounds can be administered to the animals before, during or after the food intake.

Oral administration together with the feed and/or drinking water is advisable, the active compounds being added to the total amount or only to parts of the feed and/or drinking water, depending on the requirement.

The active compounds can be added to the feed and/or the drinking water according to customary methods by simple mixing as the pure substances, preferably in the finely divided form, or in the formulated form mixed with edible, non-toxic excipients, and optionally also in the form of a premix or a feed concentrate.

The feed and/or drinking water can, for example, contain the active compounds according to the invention in a concentration from about 0.001 to 5.0%, in particular 0.02 to 2.0% (weight). The optimum level of the concentration of the active compound in the feed and/or drinking water depends, in particular, on the amount of feed and/or drinking water intake of the animals and can be easily determined by any expert.

The nature of the feed and its composition is not important here. It is possible to use all the current, commercially available or special feed compositions, which preferably contain the customary balance of energy substances and proteins, including vitamins and mineral substances, necessary for balanced nutrition. The feed can be composed, for example, of vegetable substances, for example shredded oilcake, shredded cereal and cereal by-products, but also of hay, silage fodder, beets, and other forage plants, of animal substances, for example meat and fish products, bonemeal, fats and vitamins, for example A, D, E, K and B-complex, as well as special sources of protein, for example yeasts and certain aminoacids, and mineral substances and trace elements, such as, for example, phosphorus and iron, zinc, manganese, copper, cobalt, iodine and the like.

Premixes can preferably contain about 0.1 to 50%, in particular 0.5 to 5.0% (weight) of the active compounds of the formula I, in addition to any desired edible excipients and/or mineral salts, for example carbonated feed lime, and are prepared by the customary mixing methods.

Mixed feeds preferably contain 0.001 to 5.0%, in particular 0.02 to 2.0% (weight) of the active compounds of the formula I, in addition to the customary raw material components of a mixed feed, for example shredded cereal or cereal by-products, shredded oilcake, animal protein, minerals, trace elements and vitamins. They can be prepared by the customary mixing methods.

The active compounds in premixes and mixed feed agents can preferably also be appropriately protected from air, light and/or moisture by suitable agents which cover their surface, for example with non-toxic waxes or gelatine.

The following is an example of the composition of a finished mixed feed, for poultry, containing an active compound according to the invention: 200 g of wheat, 340 g of maize, 360.3 g of coarse soya bean meal, 60 g of beef tallow, 15 g of dicalcium phosphate, 10 g of calcium carbonate, 4 g of iodinated sodium chloride, 7.5 g of a vitamin/mineral mixture and 3.2 g of an active compound premix give, after careful mixing, 1 kg of feed.

The vitamin/mineral mixture consists of: 6,000 I.U. of vitamin A, 1,000 I.U. of vitamin $D_3$, 10 mg of vitamin E, 1 mg of vitamin $K_3$, 3 mg of riboflavin, 2 mg of pyridoxine, 20 mg of vitamin $B_{12}$, 5 mg of calcium pantothenate, 30 mg of nicotinic acid, 200 mg of choline chloride, 200 mg of $MnSO_2 \times H_2O$, 140 mg of $ZnSO_4 \times 7H_2O$, 100 mg of $FeSO_4 \times 7H_2O$ and 20 mg of $CuSO_4 \times 5H_2O$. The active compound premix contains, for example, 1-desoxynijirimycin in the desired amount, for example, 1,600 mg, and in addition 1 g of DL-methionine and enough soya bean flour to form 3.2 g of premix.

The following is an example of the composition of a mixed feed, for pigs, which contains an active compound of the formula I: 630 g of shredded cereal feed (composed of 200 g of shredded maize, 150 g of shredded barley, 150 g of shredded oats and 130 g of shredded wheat), 80 g of fishmeal, 60 g of coarse soya bean meal, 58.8 g of tapioca flour, 38 g of brewer's yeast, 50 g of a vitamin/mineral mixture for pigs (composition, for example, as in the chicken feed), 30 g of linseed cake meal, 30 g of maize gluten feed, 10 g of soya bean oil, 10 g of cane sugar molasses and 2 g of active compound premix (composition, for example, as in the chicken feed), give, after careful mixing, 1 kg of feed.

The feed mixtures indicated are intended, preferably for rearing and fattening chickens or pigs respectively; however, they can also be used, in an identical or similar composition, for rearing and fattening other animals.

As already mentioned, the inhibitors can be used individually or also in any desired mixtures with one another, both the pure active compounds and the crude active compounds obtained in the preparation, optionally after a course purification, being employed.

The following Examples illustrate the invention:

EXAMPLE 1

If a 1 liter conical flask containing 120 ml of a nutrient solution of the composition
2.0% of maize starch
1.0% of glucose
0.5% of casein hydrolysate
1.0% of yeast extract
pH adjusted to 7.2 with $Na_2CO_3$
+0.4% of $CaCO_3$
sterilisation for 30' at 121° C.,
is inoculated with a spore suspension of the strain DSM 704 and the flask is incubated at 28° C. on a rotary shaking machine, after 5 days the culture solution exhibits an activity of 70 SIU/ml.

EXAMPLE 2 if a 1 liter conical flask containing 120 ml of a nutrient solution of the composition
7.5% of malt extract
0.3% of casein hydrolysate
0.7% of yeast extract
0.3% of $CaCO_3$
0.3% of $K_2HPO_4$
tap water, sterilisation for 30' at 121° C.
pH adjusted to 6.6–6.8 with $K_2CO_3$ after the sterilisation
is inoculated with a spore suspension of the strain DSM 7C4 and the flask is incubated at 28° C. on a rotary shaking machine, after 5 days the culture solution exhibits an activity of 197 SIU/ml.

EXAMPLE 3—Nutrient solution $S_3$

If a 140 liter fermenter containing 100 liters of nutrient solution of the composition
7.5% of malt extract
0.3% of casein hydrolysate
0.7% of yeast extract
0.3% of $CaCO_3$
0.3% of $K_2HPO_4$
tap water, sterilisation for 30' at 121° C.,
pH adjusted to 6.6–6.8 with $K_2CO_3$ after the sterilisation
is inoculated with 1.2 liters of a pre-culture, obtained by incubating 10 1 liter conical shaking flasks each containing 120 ml of nutrient solution of the same composition, inoculated with the strain DSM 704, and the fermenter is incubated for 5 days at 28° C., whilst stirring and with aeration, a culture broth which contains 260 SIU/ml is obtained.

EXAMPLE 4—Nutrient solution A

If a 1 liter conical flask containing 120 ml of a nutrient solution of the composition
3.0% of soya bean flour
3.0% of glycerol
0.2% of $CaCO_3$
tap water
sterilisation for 30' at 121° C.
in inoculated with a spore suspension of the strain DSM 7 and the flash is incubated at 28° C. on a rotary shaking machine, after 4 days the culture solution exhibits an activity of 437 SIU/ml.

EXAMPLE 5

If a 1 liter conical flask containing 120 ml of a nutrient solution according to Example 1 is inoculated with a spore suspension of the strain DSM 7 and the flask is incubated at 28° C. on a rotary shaking machine, after 5 days the culture solution exhibits an activity of 162 SIU/ml.

EXAMPLE 6

If a 1 liter conical flask containing 120 ml of a nutrient solution of the composition
1.0% of glucose
1.0% of soluble starch
0.5% of casein hydrolysate
0.75% of meat extract
0.75% of peptones
0.5% of yeast extract
0.1% of $K_2HPO_4$
0.3% of NaCl
0.1% of $MgSO_4.7H_2O$
tap water, pH adjusted to 7.2 with $Na_2CO_3$
sterilisation: 30' at 121° C.
is inoculated with a spore suspension of the strain DSM 7 and the flask is incubated at 28° C. on a rotary shaking machine, after 5 days the culture solution exhibits an activity of 36.4 SIU/ml.

EXAMPLE 7

If a 1 liter conical flask containing 200 ml of a nutrient solution according to Example 3 is inoculated with a spore suspension of the strain DSM 7 and the flask is incubated at 28° C. on a rotary shaking machine, after 6 days the culture solution exhibits an activity of 224 SIU/ml.

EXAMPLE 8

If a 140 liter fermenter containing 100 liters of nutrient solution according to Example 4 is inoculated with 1.2 liters of pre-culture, obtained by incubating 10 1 liter conical shaking flasks each containing 120 ml of nutrient solution of the same composition, inoculated with the strain DSM 7, and the fermenter is incubated for 5 days at 28° C., whilst stirring and with aeration, a culture broth which contains 286 SIU/ml is obtained.

EXAMPLE 9

If a 1 liter conical flask containing 120 ml of a nutrient solution according to Example 2 is inoculated with a spore suspension of the strain DSM 1 and the flask is incubated at 28° C. on a rotary shaking machine, after 6 days the culture solution exhibits an activity of 28.4 SIU/ml.

EXAMPLE 10

If a 1 liter conical flask containing 120 ml of a nutrient solution according to Example 1 is inoculate with a spore suspension of the strain DSM 365 and the flask is incubated at 28° C. on a rotary shaking machine, after 4 days the culture solution exhibits an activity of 15.6 SIU/ml.

EXAMPLE 11

If a 1 liter conical flask containing 120 ml of a nutrient solution according to Example 2 is inoculated with a spore suspension of the strain DSM 365 and the flask is incubated at 28° C. on a rotary shaking machine, after 4 days the culture solution exhibits an activity of 25.8 SIU/ml.

EXAMPLE 12

If a 1 liter conical flask containing 120 ml of a nutrient solution according to Example 4 is inoculated with a spore suspension of the strain DSM 741 and the flask is incubated at 28° C. on a rotary shaking machine, after 5 days the culture solution exhibits an activity of 3.2 SIU/ml.

EXAMPLE 13

If a 1 liter conical flask containing 120 ml of a nutrient solution of the composition according to Example 1 is inoculated with a spore suspension of the strain DSM 741 and the flask is incubated at 28° C. on a rotary shaking machine, after 5 days the culture solution exhibits an activity of 26.4 SIU/ml.

EXAMPLE 14

If a 1 liter conical flask containing 120 ml of a nutrient solution of the composition according to Example 2 is inoculated with a spore suspension of the strain DSM 741 and the flask in incubated at 28° C. on a rotary shaking machine after 3 days the culture solution exhibits an activity of 24.0 SIU/ml.

EXAMPLE 15

If a 1 liter conical flask containing 120 ml of a nutrient solution of the composition
 2.0% of maize starch
 0.5% of glucose
 0.3% of casein hydrolysate
 pH adjusted to 7.2 with $Na_2CO_3$
 +0.4% of $CaCO_3$
 sterilisation: 30' at 121° C.
is inoculated with a spore suspension of the strain DSM 741 and the flask is incubated at 28° C. on a rotary shaking machine, after 2 days the culture solution exhibits an activity of 81.7 SIU/ml and after 3 days it exhibits an activity of 121 SIU/ml.

EXAMPLE 16

If a 1 liter conical flask containing 120 ml of a nutrient solution according to Example 4 is inoculated with a spore suspension of the strain DSM 675 and the flask is incubated at 28° C. on a rotary shaking machine, after 5 days the culture solution exhibits an activity of 8.6 SIU/ml.

EXAMPLE 17

If a 1 liter conical flask containing 120 ml of a nutrient solution according to Example 1 is inoculated with a spore suspension of the strain DSM 675 and the flask is incubated at 28° C. on a rotary shaking machine, after 5 days the culture solution exhibits an activity of 53.0 SIU/ml.

EXAMPLE 18

If a 1 liter conical flask containing 120 ml of a nutrient solution according to Example 2 is inoculated with a spore suspension of the strain DSM 675 and the flask is incubated at 28° C. on a rotary shaking machine, after 4 days the culture solution exhibits an activity of 17.8 SIU/ml.

EXAMPLE 19

It a 1 liter conical flask containing 120 ml of a nutrient solution according to Example 4 is inoculated with a spore suspension of the strain DSM 372 and the flask is incubated at 28° C. on a rotary shaking machine, after 5 days the culture solution exhibits an activity of 6.0 SIU/ml.

EXAMPLE 20

If a 1 liter conical flask containing 120 ml of a nutrient solution according to Example 1 is inoculated with a spore suspension of the strain DSM 372, and the flask is incubated at 28° C. on a rotary shaking machine, after 4 days the culture solution exhibits an activity of 21.6 SIU/ml.

EXAMPLE 21

If a 1 liter conical flask containing 200 ml of a nutrient solution according to Example 2 is inoculated with a spore suspension of the strain DSM 372 and the flask is incubated at 28° C. on a rotary shaking machine, after 3 days the culture solution exhibits an activity of 26.8 SIU/ml.

EXAMPLE 22

If a 1 liter conical flask containing 120 ml of a nutrient solution of the composition
 2.0% of maize starch
 1.0% of glucose
 0.5% of casein hydrolysate
 0.5% of yeast extract
 pH adjusted to 7.2 with $Na_2CO_3$
 +0.4% of $CaCO_3$
 sterilisation: 30' at 121° C.
is inoculated with a spore suspension of the strain DSM 372 and the flask is incubated at 28° C. on a rotary shaking machine, after 3 days the culture solution exhibits an activity of 26.5 SIU/ml.

EXAMPLE 23

If a 1 liter conical flask containing 120 ml of a nutrient solution according to Example 22 is inoculated with a spore suspension of the strain DSM 479 and the flask is incubated at 28° C. on a rotary shaking machine, after 3 days the culture solution exhibits an activity of 7.9 SIU/ml.

EXAMPLE 24

If a 1 liter conical flask containing 120 ml of a nutrient solution according to Example 6 is inoculated with a spore suspension of the strain DSM 36 and the flask is incubated at 28° C. on a rotary shaking machine, after 3 days the culture solution exhibits an activity of 5.4 SIU/ml.

EXAMPLE 25

If a 1 liter conical flask containing 120 ml of a nutrient solution according to Example 2 is inoculated with a spore suspension of the strain DSM 36 and the flask is incubated at 28° C. on a rotary shaking machine after 3 days the culture solution exhibits an activity of 5.4 SIU/ml.

EXAMPLE 26

If a 1 liter conical flask containing 120 ml of a nutrient solution according to Example 2 is inoculated with a spore suspension of the strain DSM 356 and the flask is incubated at 28° C. on a rotary shaking machine after 3 days the culture solution exhibits an activity of 8.8 SIU/ml.

EXAMPLE 27

If a 1 liter conical flask containing 120 ml of a nutrient solution according to Example 1 is inoculated with a spore suspension of the strain DSM 292 and the flask is incubated at 28° C. on a rotary shaking machine after 3 days the culture solution exhibits an activity of 9.0 SIU/ml.

EXAMPLE 28

If a 1 liter conical flask containing 120 ml of a nutrient solution according to Example 2 is inoculated with a spore suspension of the strain DSM 292 and the flask is incubated at 28° C. on a rotary shaking machine after 3 days the culture solution exhibits an activity of 9.2 SIU/ml.

EXAMPLE 29

If a 1 liter conical flask containing 120 ml of a nutrient solution according to Example 2 is inoculated with a spore suspension of the strain DSM 742 and the flask is incubated at 28° C. on a rotary shaking machine after 3 days the culture solution exhibits an activity of 9.8 SIU/ml.

EXAMPLE 30

If a 1 liter conical flask containing 120 ml of a nutrient solution according to Example 1 is inoculated with a spore suspension of the strain DSM 740 and the flask is incubated at 28° C. on a rotary shaking machine after 4 days the culture solution exhibits an activity of 5.7 SIU/ml.

EXAMPLE 31

The fermentation broth from a 100 liter fermenter according to Example 3 was adjusted to pH 3.0-3.5 with half-concentrated HCl and, after flocculating, the bacterial mass is centrifuged off. 70 liters of a deep brown culture solution with a SIU content of 220,000 SIU/liter are obtained. This solution was passed with a flow rate of 20 l/hour over a column of $\phi$ 30 cm packed with 12 kg of Lewatit(®) $SC$ 104 on the H+ form. The permeate had virtually no saccharase inhibitory activity and was discarded. The column was washed with 50 l of distilled $H_2O$ (wash water I), 20 l of 0.01 N HCl and then again with 20 l of distilled $H_2O$ (wash water II). 2.5% strength ammonia now followed, for desorption of the activity. The saccharase-inhibitory activity is eluted, parallel with the rise in the conductivity of the eluate and the increase in the brown coloration. The first runnings (20 l) up to the rise in the conductivity are discarded and the fraction containing the activity (35 l) is concentrated in a rotary evaporator and redissolved in a little water (concentrate, 3 l). The concentrate was lyophilised. 288 g of a deep brown crude product I of 38,000 SIU/g were obtained.

EXAMPLE 32

The fermentation broth from a 100 liter fermenter according to Example 8 was adjusted to pH 3.0-3.5 with half-concentrated HCl and, after flocculating, the bacterial mass was centrifuged off. 60 liters of a deep brown culture solution with a SIU content of 240,000 SIU/liter were obtained. This solution was passed with a flow rate of 20 l/hour over a column of $\phi$ 30 cm packed with 12 kg of Dowex 50 W×4 in the H+form. The permeate had virtually no saccharase-inhibitory activity and was discarded. The column was washed with 50 l of distilled $H_2O$ (wash water I), 20 l of 0.01 N HCl and then again with 20 l of distilled $H_2O$ (wash water II). 2.5% strength ammonia now followed for desorption of the activity. The saccharase-inhibitory activity is eluted, parallel with the rise in the conductivity of the eluate and the increase in the brown coloration. The first runnings (20 l) up to the rise in the conductivity are discarded and the fraction containing the activity (35 l) is concentrated in a rotary evaporator and redissolved in a little water (concentrate, 3 l). The concentrate was lyophilised. 360 g of a deep brown crude product I of 24,000 SIU/g were obtained.

EXAMPLE 33

50 g of the crude product I from Example 31 were finely ground in a mortar and then extracted 3× with 300 ml of technical grade methanol each time. For this, the batch was first homogenised for 2 minutes in an Ultraturraxhomogeniser then put in a water bath, warmed to 40°-50° C., and stirred for 20°. After each extraction the mixture was filtered through a fluid filter. The residue remaining on the fluted filter after the 3rd extraction was dried in vacuo (28.4 g). Since testing showed only a low specific activity of this residue, it was then discarded. The methanolic extracts were combined and concentrated to dryness in vacuo. The active residue remaining in the flask was dissolved in 750 ml of $H_2O$ (L=2.8 mS, pH=7.2) and the solution was passed with a flow rate of 500 ml/hour over a 5×50 cm column packed with CM cellulose in the H+ form (CH cellulose from Messrs. Whatman, type C 52). The column was rinsed with 5 l of water and this was followed with 20 l of 0.002 N HCl for the elution. The permeate, wash water and eluate were franctionally collected in approximately 0.5 l portions. The saccharase-inhibitory activity was determined and all fractions which contained more than 30,000 SIU/l were combined; in the permeate these were the deep brown-coloured fractions 2-4 and in the light yellow eluate the fractions 16-35. The combined fractions were concentrated and lyophilised. 18.2 g of the permeate fraction 2-4 with a specific activity of 4,000 SIU/g (discarded) and 3.1 g of the so-called crude product II of 250,000 SIU/g (about 50-60% pure) were obtained. The crude product II is strongly hygroscopic and deliquesces in air in a short time to give a sticky mass.

EXAMPLE 34

In order to separate off the majority of the accompanying peptides, 2.5 g of the crude product II from Example 33 are dissolved in 15 ml of methanol and chromatographed over a 5×90 cm column packed with Sephadex LH 20 in methanol. 10 ml of fractions are collected at a flow rate of 100 ml/hour and a temperature of 4°-5° C. 10 μl of these fractions are applied to a silica gel plate (Messrs. Merck) and investigated by thin layer chromatography in the system ethanol/25% strength $NH_3/H_2O$=80/10/10. The fractions which, according to thin layer chromatography, contained inhibitor were combined, concentrated to 5-10 ml and re-chromatographed over the same column. The fractions were analyzed by thin layer chromatography and the fractions containing inhibitor were combined, only a very narrow range having been cut. The combined fractions are concentrated to dryness. The inhibitor purified with LH 20 in this way is about 90% pure. In order to separate off the last remaining peptide impurities, the substance remaining as the residue, after evaporation in a rotary evaporator, is taken up in 2-3 ml of methanol and 50 μl of concentrated HCl are added to the yellow methanolic solution. After a short time, if appropriate even only after standing for several hours, the inhibitor crystallises out in the form of slightly yellowish cubes or parallelepipeds. The peptides remain in the mother liquor. The crystals are centrifuged off and washed once with ice-cold methanol and the washed precipitate is then dissolved again in 2 ml of methanol, whilst heating. 4 ml of butanol are added and the mixture is stored at 4° C. overnight. The colourless crystals which have precipitated by the next morning are centrifuged off, washed once with ice-cold methanol, once with acetone and once with ether and then dried in vacuo. Yield: 460 mg of the inhibitor in the form of hydrochloride, of 540,000 SIU/g.

EXAMPLES 35 to 42

In order to detect saccharase-inhibitory components inthe culture solution or crude products, in each of these Examples, the following thin layer chromatography process with a subsequent enzyme reaction on the plate, which enabled inhibitory components to be detected directly on the plate, was also used. In this thin layer chromatography, 1-5 μl of the fermentation broth or 1-5 μg of the formulations are applied to silica gel finished plates (Messrs. Merck, type KG 60 F 254) and the plate is developed in ethanol/$NH_3$/$H_2O$ = 8/1/1. (I) or ethyl acetate/methanol/water = 10/6/4 (II). In order to make the saccharase-inhibitory components visible directly, the developed and thoroughly dried plate is sprayed with enzyme gel (20 ml/20×20 cm plate) and the gel is allowed to solidify. The plate is then pre-incubated for 5' in a moist chamber at room temperature and then sprayed to saturation with substrate gel. After this 2nd gel layer has solidified, the plate is introduced into a moist chamber and incubated at 40° C. The inhibition coloration (light spots, red-brown background) develops in the course of 60-90'. The incubation is interrupted at the point in time of optimum colour development and the plate, with the agar layers on it, is dried with warm air from a fan.

Preparation of the gels:

Enzyme gel: 1.5 g of agarose (L'Industrie Biologique Francais) is suspended in 10 ml of 0.2 M Na maleate buffer of pH 6.0 and then dissolved by boiling. The clear agarose solution is cooled to 50° C. and 250 μl of Triton X-100 solution (2 g of Triton X-100 + 8 g of ethanol, analytical grade) and 0.5 ml of dianisidine solution (20 mg of dianisidine/1 ml of acetone) are added, whilst swirling. 1 ml of GOD/POD reagent (12.5 mg of glucose oxidase, degree of purity I, Messrs. Böhringer order No. 15,423, and 2.5 mg of peroxidase, degree of purity II, Messrs. Böhringer, order No. 15,302, dissolved in 5 ml of maleate buffer) and 4-5 units of saccharase from the swine small intestine (as described previously in the saccharase inhibition test) are added directly before the gel is used. The gel must be kept at 50° C. until the spraying, since it otherwise solidifies in the jets during the spraying operation. Substrate gel: 0.5 g of agarose is suspended in 100 ml of Na maleate buffer of pH 6.0 and dissolved, whilst boiling. The solution is then cooled to 50° C., 100 μl of Triton (2 g of Triton X-100 + 8 g of ethanol, analytical grade) and 1 g of sucrose (Serva No. 35,579) are added. After dissolving the sucrose, the gel is ready to use.

The investigation of the culture solutions of the strains using this method gave saccharase-inhibitory components with the following $R_f$ values in system I

| Example No. | Strains | $R_f$ values |
|---|---|---|
| 35 | DSM 7 | 0.25 |
| 36 | DSM 741 | 0.25; 0.41; 0.50; 0.59 and 0.71 |
| 37 | DSM 704 | 0.25 |
| 38 | DSM 372 | 0.25; 0.51; 0.60 and 0.71 | and the following $R_f$ values in system II

| Example No. | Strains | $R_f$ values |
|---|---|---|
| 39 | DSM 704 | 0.05 |
| 40 | DSM 479 | (0.05); 0.22–0.35; 0.62–0.67 and 0.88 |
| 41 | DSM 741 | (0.05); 0.23–0.35 and 0.62–0.67 |
| 42 | DSM 372 | (0.05) 0.20–0.22 |

EXAMPLE 43

If a 1 liter conical flask containing 120 ml of a nutrient solution of the composition 1.0% of starch
0.1% of glucose
0.5% of casein hydrolysate
1.0% of yeast extract
pH adjusted to 7.2 with $Na_2CO_3$
+0.4% of $CaCO_3$
sterilization : 30' at 121° C.

is inoculated with a spore suspension of the strain DSM 479 and the flask is incubated at 28° C. on a rotary shaking machine, after 2 days the culture solution exhibits an activity of 20.2 SIU/ml.

EXAMPLE 44

If a 1 liter conical flask containing 120 ml of a nutrient solution of the composition 2.0% of maize starch
1.0% of glucose
0.5% of casein hydrolysate
1.0% of yeast extract
0.1% of $K_2HPO_4$
pH adjusted to 7.2 with $Na_2CO_3$
+0.4% of $CaCO_3$
sterilisation: 30' at 121° C.

is inoculated with a spore suspension of the strain DSM 372 and the flask is incubated at 28° C. on a rotary shaking machine, after 2.5 days the culture solution exhibits an activity of 50.3 SIU/ml.

EXAMPLES 45 TO 69

In each of these examples 1 liter conical flasks containing 120 ml of a nutrient solution of the composition according to Examples 1, 2, 4 or 6, as indicated in the Table are inoculated with spore suspensions of the strains listed and the flasks are incubated at 28° C. on rotary shaking machines after 4 days the culture solutions exhibit the activities shown in the Table:

| Example No. | Strain | Nutrient solution according to Example | Activity of the culture solution after 4 days in SIU/ml |
|---|---|---|---|
| 45 | KA-63 DSM 1060 | 4 | 31 |
| 46 | " | 1 | 6.6 |
| 47 | " | 6 | 25 |
| 48 | " | 2 | 7.9 |
| 49 | IAM 1523 DSM 1061 | 4 | 50 |
| 50 | " | 1 | 4.3 |
| 51 | " | 6 | 3.8 |
| 52 | " | 2 | 2.7 |
| 53 | OUT 8108 DSM 1062 | 4 | 8.4 |
| 54 | " | 1 | 3.6 |
| | " | 2 | 3.1 |
| 55 | OUT 8110 DSM 1063 | 4 | 28 |
| 56 | " | 1 | 71 |
| 57 | " | 6 | 69 |
| 58 | " | 2 | 104 |
| 59 | S 202 DSM 1064 | 4 | 38 |
| 60 | " | 1 | 10.6 |
| 61 | " | 2 | 14.4 |
| 62 | S 204 DSM 1065 | 4 | 54 |
| 63 | " | 1 | 2.7 |
| 64 | S 219 DSM 1066 | 4 | 28 |
| 65 | " | 1 | 1.5 |
| 66 | " | 2 | 10.3 |
| 67 | S 242 DSM 1067 | 1 | 17 |
| 68 | " | 4 | 3.8 |
| 69 | " | 2 | 4.1 |

What is claimed is:

1. A method of producing an inhibitor for glycoside hydrolases which comprises culturing an organism of the family Bacillaceae capable of producing said inhibitor in a nutrient solution at about 15°–40° C. for non-thermophilic Bacilli and 15°–80° C. for thermophilic Bacilli containing a source of nitrogen, a source of carbon and a nutrient salt for a time sufficient to produce said inhibitor then separating said glycoside hydrolase inhibitor from the culture, wherein said inhibitor is: a. readily soluble in water; b. stable towards heat at neutral pH values; c. stable towards acid at pH of 2; d. stable towards alkali at pH of 12; e. dialysable; if. not inactivated by trypsin or pepsin; g. not an inhibitor for trypin or pepsin; h. not stainable with typical protein dyestuffs; and i. of a molecular weight over 100 but below 2000

2. A method according to claim 1 wherein the micro-organism is of the genus Bacillus.

3. A method according to claim 1 wherein the organism is of the species *B. subtilis, B. subtilis var. niger, B. amyloliquefaciens, B. coagulans, B. longisporus* and *B. polymyxa.*

4. A method according to claim 1 wherein the micro-organism is of the strain DSM 292, DSM 356, DSM 36, DSM 740, DSM 741, DSM 1, DSM 479, DSM 365, DSM 742, DSM 7, DSM 372 or DSM 675, DSM 704.

5. A method according to claim 1 wherein the organism is cultured in a nutrient solution at a temperature of from 15° to 80° C. for from 1 to 8 days, with aeration, the cells are centrifuged off and the inhibitors are isolated from the culture broth or from the cell extracts.

6. A method according to claim 1 wherein the organism is of the strain DSM 1060, DSM 1061, DSM 1062, DSM 1063, DSM 1064, DSM 1065, DSM 1066, or DSM 1067.

7. A method of producing 1-desoxynojirimycin which comprises culturing a 1-desoxynojirimycin producing organism of the genus Bacillus in a nutrient solution at about 15°–40° C. for non-thermophilic Bacilli and 15°–80° C. for thermophilic Bacilli containing a source of nitro, a source of carbon and a nutrient salt for a time sufficient to produce said 1-desoxynojirimycin, then separating 1-desoxynojirimycin from the culture.

8. A method of producing 1-desoxynojirimycin according to claim 5 which comprises culturing a micro-organism of the strain DSM 7, DSM 704, DSM 675 or DSM 372.

9. An in vitro biologically pure culture of a glycoside-hydrolase-inhibiting producing micro-organism of the genus Bacillus, strain DSM 704, DSM 740, DSM 741 or DSM 742.

* * * * *